US011059025B2

(12) United States Patent
Lee et al.

(10) Patent No.: US 11,059,025 B2
(45) Date of Patent: Jul. 13, 2021

(54) SUPER ABSORBENT RESIN

(71) Applicant: LG Chem, Ltd., Seoul (KR)

(72) Inventors: Sang Gi Lee, Daejeon (KR); Hye Mi Nam, Daejeon (KR); Min Ho Hwang, Daejeon (KR); Soo Jin Lee, Daejeon (KR); Tae Hwan Jang, Daejeon (KR)

(73) Assignee: LG Chem, Ltd.

( * ) Notice: Subject to any disclaimer, the term of this patent is extended or adjusted under 35 U.S.C. 154(b) by 946 days.

(21) Appl. No.: 15/558,429

(22) PCT Filed: Jun. 1, 2016

(86) PCT No.: PCT/KR2016/005809
§ 371 (c)(1),
(2) Date: Sep. 14, 2017

(87) PCT Pub. No.: WO2016/195376
PCT Pub. Date: Dec. 8, 2016

(65) Prior Publication Data
US 2018/0056274 A1  Mar. 1, 2018

(30) Foreign Application Priority Data

Jun. 1, 2015 (KR) .......................... 10-2015-0077534
May 31, 2016 (KR) .......................... 10-2016-0067426

(51) Int. Cl.

| | |
|---|---|
| B01J 20/26 | (2006.01) |
| B01J 20/30 | (2006.01) |
| B01J 20/28 | (2006.01) |
| C08J 3/24 | (2006.01) |
| C08J 3/075 | (2006.01) |
| C08J 9/08 | (2006.01) |
| C08J 9/20 | (2006.01) |
| C08F 6/00 | (2006.01) |
| A61L 15/22 | (2006.01) |
| C08J 9/00 | (2006.01) |
| C08J 9/224 | (2006.01) |
| C08F 2/44 | (2006.01) |
| A61L 15/60 | (2006.01) |
| C08J 3/12 | (2006.01) |
| C08G 77/46 | (2006.01) |

(52) U.S. Cl.
CPC ............. *B01J 20/267* (2013.01); *A61L 15/22* (2013.01); *A61L 15/60* (2013.01); *B01J 20/261* (2013.01); *B01J 20/265* (2013.01); *B01J 20/28004* (2013.01); *B01J 20/28016* (2013.01); *B01J 20/28047* (2013.01); *B01J 20/3021* (2013.01); *B01J 20/3064* (2013.01); *B01J 20/3078* (2013.01); *B01J 20/3085* (2013.01); *C08F 2/44* (2013.01); *C08F 6/008* (2013.01); *C08J 3/075* (2013.01); *C08J 3/12* (2013.01); *C08J 3/245* (2013.01); *C08J 9/0061* (2013.01); *C08J 9/0066* (2013.01); *C08J 9/08* (2013.01); *C08J 9/20* (2013.01); *C08J 9/224* (2013.01); *B01J 2220/68* (2013.01); *C08G 77/46* (2013.01); *C08J 2201/026* (2013.01); *C08J 2203/02* (2013.01); *C08J 2203/10* (2013.01); *C08J 2205/022* (2013.01); *C08J 2333/02* (2013.01); *C08J 2333/04* (2013.01); *C08J 2483/12* (2013.01)

(58) Field of Classification Search
CPC .......................... B01J 20/267; B01J 20/28004
See application file for complete search history.

(56) References Cited

U.S. PATENT DOCUMENTS

| | | | |
|---|---|---|---|
| 4,883,478 A | 11/1989 | Lerailler et al. | |
| 4,973,632 A | 11/1990 | Nagasuna et al. | |
| 5,032,628 A | 7/1991 | Choi et al. | |
| 5,118,719 A | 6/1992 | Lind | |
| 5,328,935 A | 7/1994 | Van Phan et al. | |
| 5,563,218 A | 10/1996 | Rebre et al. | |
| 5,712,316 A | 1/1998 | Dahmen et al. | |
| 5,985,944 A | 11/1999 | Ishizaki et al. | |
| 6,107,358 A | 8/2000 | Harada et al. | |
| 6,133,193 A | 10/2000 | Kajikawa et al. | |
| 6,174,929 B1 | 1/2001 | Hahnle et al. | |
| 6,414,214 B1 | 7/2002 | Engelhardt et al. | |
| 6,565,768 B1 | 5/2003 | Dentler et al. | |
| 6,750,262 B1 | 6/2004 | Hahnle et al. | |
| 7,638,570 B2 * | 12/2009 | Torii | A61L 15/60 524/430 |
| 7,803,880 B2 * | 9/2010 | Torii | C08F 20/06 525/329.7 |

(Continued)

FOREIGN PATENT DOCUMENTS

| | | |
|---|---|---|
| CN | 1856331 A | 11/2006 |
| CN | 101094696 A | 12/2007 |

(Continued)

OTHER PUBLICATIONS

Extended European Search Report including Written Opinion for Application No. EP16890123.9 dated Sep. 7, 2018.
Third Party Observation for PCT/KR2016/006202 dated Oct. 16, 2017.
Kabiri, K, et al.., "Novel approach to highly porous superabsorbent hydrogels: synergistic effect of porogens on porosity and swelling rate." Polymer International, vol. 52, Jan. 7, 2003, pp. 1158-1164.
Kabiri, Kourosh, et al. "Porous Superabsorbent Hydrogel Composites: Synthesis, Morphology and Swelling Rate." Macromolecular Materials and Engineering, Apr. 20, 2004, vol. 289, pp. 653-661.
Odian, George, "Principle of Polymerization." Second Edition, (Wiley, 1981), p. 203.

(Continued)

*Primary Examiner* — Yong L Chu
(74) *Attorney, Agent, or Firm* — Lerner, David, Littenberg, Krumholz & Mentlik, LLP

(57) ABSTRACT

The present invention relates to a super absorbent resin, and the super absorbent resin can exhibit a fast absorption rate and high gel strength even in a partially swollen state through the size optimization of partially swollen gel particles. Therefore, the use of the super absorbent resin can effectively prevent a rewetting phenomenon.

8 Claims, 3 Drawing Sheets

(56) References Cited

U.S. PATENT DOCUMENTS

| | | |
|---|---|---|
| 2001/0038831 A1 | 11/2001 | Park et al. |
| 2004/0019342 A1 | 1/2004 | Nagasuna et al. |
| 2004/0214946 A1 | 10/2004 | Smith et al. |
| 2005/0054784 A1 | 3/2005 | Qin et al. |
| 2005/0137546 A1 | 6/2005 | Joy et al. |
| 2005/0256469 A1 | 11/2005 | Qin et al. |
| 2006/0204755 A1 | 9/2006 | Torii et al. |
| 2007/0066167 A1 | 3/2007 | Wada et al. |
| 2007/0123658 A1 | 5/2007 | Torii et al. |
| 2007/0141338 A1 | 6/2007 | Ishizaki et al. |
| 2008/0058747 A1 | 3/2008 | Singh Kainth et al. |
| 2008/0139693 A1 | 6/2008 | Ikeuchi et al. |
| 2008/0161499 A1 | 7/2008 | Riegel et al. |
| 2008/0215026 A1 | 9/2008 | Schornick et al. |
| 2008/0234645 A1 | 9/2008 | Dodge et al. |
| 2009/0196848 A1 | 8/2009 | Davis |
| 2010/0057027 A1 | 3/2010 | Furno et al. |
| 2010/0099781 A1 | 4/2010 | Tian et al. |
| 2011/0204288 A1 | 8/2011 | Funk et al. |
| 2011/0313113 A1 | 12/2011 | Sakamoto et al. |
| 2012/0045639 A1 | 2/2012 | Whitmore et al. |
| 2012/0184670 A1 | 7/2012 | Kobayashi et al. |
| 2012/0184684 A1 | 7/2012 | Funk et al. |
| 2012/0219728 A1 | 8/2012 | Badri et al. |
| 2012/0232177 A1 | 9/2012 | Lopez Villanueva et al. |
| 2012/0258851 A1 | 10/2012 | Nakatsuru et al. |
| 2012/0296296 A1 | 11/2012 | Di Cintio et al. |
| 2012/0296297 A1 | 11/2012 | Di Cintio et al. |
| 2012/0296298 A1 | 11/2012 | Gray et al. |
| 2012/0296299 A1 | 11/2012 | Villanueva et al. |
| 2012/0309619 A1 | 12/2012 | Kwon et al. |
| 2013/0102750 A1 | 4/2013 | Watanabe et al. |
| 2013/0172180 A1 | 7/2013 | Naumann et al. |
| 2014/0066584 A1 | 3/2014 | Peterson et al. |
| 2014/0127510 A1 | 5/2014 | Handa et al. |
| 2014/0296423 A1 | 10/2014 | Ebata et al. |
| 2014/0306155 A1 | 10/2014 | Tian et al. |
| 2014/0306156 A1 | 10/2014 | Tian et al. |
| 2014/0312273 A1 | 10/2014 | Wattebled et al. |
| 2014/0364824 A1 | 12/2014 | Oda et al. |
| 2015/0011388 A1* | 1/2015 | Matsumoto ............ A61L 15/60 502/402 |
| 2015/0087742 A1 | 3/2015 | Won et al. |
| 2015/0093575 A1 | 4/2015 | Naumann et al. |
| 2015/0129799 A1 | 5/2015 | Kobayashi et al. |
| 2015/0137546 A1 | 5/2015 | Gaudig |
| 2015/0283284 A1 | 10/2015 | Azad et al. |
| 2016/0108227 A1 | 4/2016 | Wattebled et al. |
| 2016/0151531 A1 | 6/2016 | Lee et al. |
| 2016/0184799 A1 | 6/2016 | Lee et al. |
| 2018/0037686 A1 | 2/2018 | Lee et al. |
| 2018/0050321 A1* | 2/2018 | Lee ........................ B01J 20/265 |
| 2018/0056274 A1 | 3/2018 | Lee et al. |
| 2018/0079847 A1 | 3/2018 | Lee et al. |
| 2018/0265645 A1 | 9/2018 | Nam et al. |
| 2018/0265646 A1 | 9/2018 | Nam et al. |

FOREIGN PATENT DOCUMENTS

| | | |
|---|---|---|
| CN | 101133100 A | 2/2008 |
| CN | 102197057 A | 9/2011 |
| CN | 102666670 A | 9/2012 |
| CN | 102762616 A | 10/2012 |
| CN | 103179931 A | 6/2013 |
| CN | 104024291 A | 9/2014 |
| CN | 104284921 A | 1/2015 |
| CN | 104603159 A | 5/2015 |
| EP | 0555692 A1 | 8/1993 |
| EP | 0615736 A1 | 9/1994 |
| EP | 0644211 A1 | 3/1995 |
| EP | 0744435 A1 | 11/1996 |
| EP | 1400556 A1 | 3/2004 |
| EP | 1637105 A1 | 3/2006 |
| EP | 1730218 B1 | 12/2010 |
| EP | 3248990 A1 | 11/2017 |
| EP | 3260485 A1 | 12/2017 |
| EP | 2797566 B1 | 6/2019 |
| JP | H06313042 A | 11/1994 |
| JP | H09124879 A | 5/1997 |
| JP | H10139916 A | 5/1998 |
| JP | H10251309 A | 9/1998 |
| JP | H11156188 A | 6/1999 |
| JP | 2005154758 A | 6/2005 |
| JP | 2006116535 A | 5/2006 |
| JP | 20070012623 | 1/2007 |
| JP | 3913867 B2 | 5/2007 |
| JP | 2007314794 A | 12/2007 |
| JP | 2009227885 A | 10/2009 |
| JP | 2011511086 A | 4/2011 |
| JP | 5336704 B2 | 11/2013 |
| JP | 2014098172 A | 5/2014 |
| JP | 2014514128 A | 6/2014 |
| JP | 2014514432 A | 6/2014 |
| JP | 2014518716 A | 8/2014 |
| JP | 2014523452 A | 9/2014 |
| JP | 2015503655 A | 2/2015 |
| JP | 2015150059 A | 8/2015 |
| JP | 2015213911 A | 12/2015 |
| KR | 910008293 B1 | 10/1991 |
| KR | 930007272 B1 | 8/1993 |
| KR | 100269980 B1 | 10/2000 |
| KR | 20050022813 A | 3/2005 |
| KR | 20060015498 A | 2/2006 |
| KR | 20060023116 A | 3/2006 |
| KR | 20090042828 A | 4/2009 |
| KR | 20090123904 A | 12/2009 |
| KR | 20110092236 A | 8/2011 |
| KR | 20120102088 A | 9/2012 |
| KR | 20130120300 A | 11/2013 |
| KR | 20140054324 A | 5/2014 |
| KR | 20140056225 A | 5/2014 |
| KR | 20140094536 A | 7/2014 |
| KR | 20140095569 A | 8/2014 |
| KR | 20140102264 A | 8/2014 |
| KR | 20140107347 A | 9/2014 |
| KR | 20150016126 A | 2/2015 |
| KR | 20150040476 A | 4/2015 |
| KR | 20150116418 A | 10/2015 |
| KR | 20150143624 A | 12/2015 |
| KR | 101582241 B1 | 1/2016 |
| KR | 20160010517 A | 1/2016 |
| WO | 87003208 A1 | 6/1987 |
| WO | 2004096304 A1 | 11/2004 |
| WO | 2005027986 A1 | 3/2005 |
| WO | 2006069732 A1 | 7/2006 |
| WO | 2011026876 A1 | 3/2011 |
| WO | 2014167040 A1 | 10/2014 |
| WO | 2014168858 A1 | 10/2014 |
| WO | 2014168871 A1 | 10/2014 |

OTHER PUBLICATIONS

Schwalm, Reinhold, "UV Coatings: Basics, Recent Developments and New Applications." Elservier Science, Dec. 21, 2016, p. 115.

Search report from International Application No. PCT/KR2016/003793, dated Dec. 22, 2016.

Search report from International Application No. PCT/KR2016/003946, dated Jul. 29, 2016.

Search report from International Application No. PCT/KR2016/003948, dated Jul. 27, 2016.

Search report from International Application No. PCT/KR2016/005809, dated Aug. 24, 20116.

Search report from International Application No. PCT/KR2016/013286, dated Mar. 6, 2017.

U.S. Appl. No. 15/554,852, filed Aug. 31, 2017.
U.S. Appl. No. 15/556,078, filed Sep. 6, 2017.
U.S. Appl. No. 15/556,083, filed Sep. 6, 2017.
U.S. Appl. No. 15/556,740, filed Sep. 8, 2017.

Third Party Observation for Application No. EP16890123.9 dated Jul. 10, 2018.

Third Party Observation for Application No. PCT/KR2016/013286 dated Jun. 25, 2018.

(56) References Cited

OTHER PUBLICATIONS

Third Party Observation for Application No. PCT/KR2016/003946 dated Oct. 31, 2017.
Third Party Observation for Application No. PCT/KR2016/003948 dated Oct. 13, 2017.
Lee at al., U.S. Appl. No. 15/564,487, filed Oct. 5, 2017, titled "Super Absorbent Polymer".
Odian, George, "Principles of Polymerization." Second Edition, Copyright 1981, p. 203.
Schwalm, Reinhold, "UV Coatings: Basics, Recent Developments and New Applications." Elsevier Science, Dec. 21, 2006, p. 115.
Search report from International Application No. PCT/KR2016/006202, dated Sep. 12, 2016.
Extended European Search Report including Written Opinion for Application No. EP16803731.5 dated Sep. 3, 2018.
Extended European Search Report including Written Opinion for Application No. EP16811803.2 dated Aug. 27, 2018.
Buchholz, et al., Modern Superabsorbent Polymer Technology, 1998, vol. 152, pp. 199-201, New York: Wiley-vch.
Third Party Observation for Application No. 16811871.9 dated Jan. 3, 2020, 7 pages.
Third Party Observation for Application No. 16890123.9 dated Jan. 3, 2020, 4 pages.
Third Party Observation for PCT/KR2016/005809 dated Sep. 29, 2017.
Extended European Search Report including Written Opinion for Application No. EP16835267.2 dated Aug. 22, 2018.

* cited by examiner

[FIG. 1]
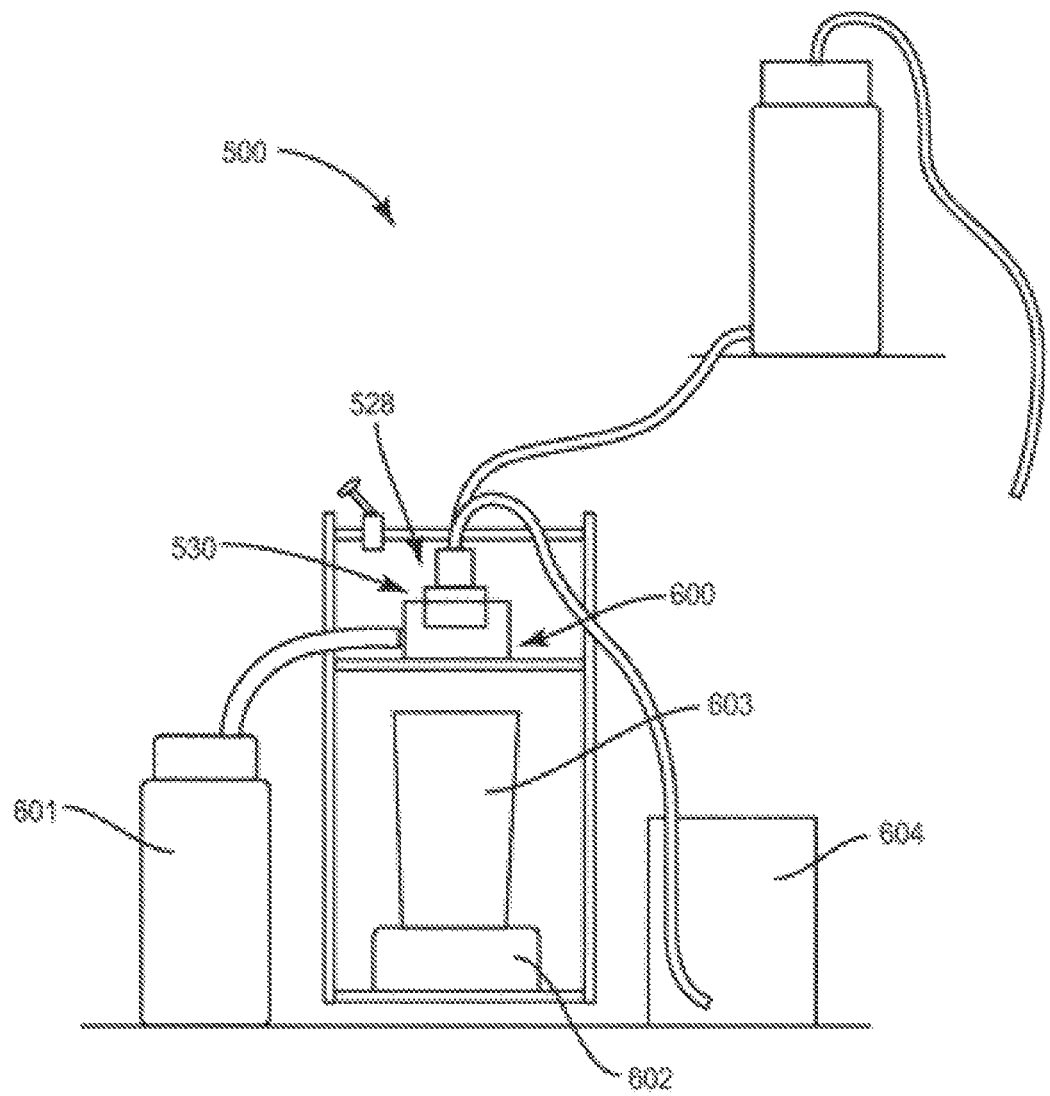

[FIG. 2]
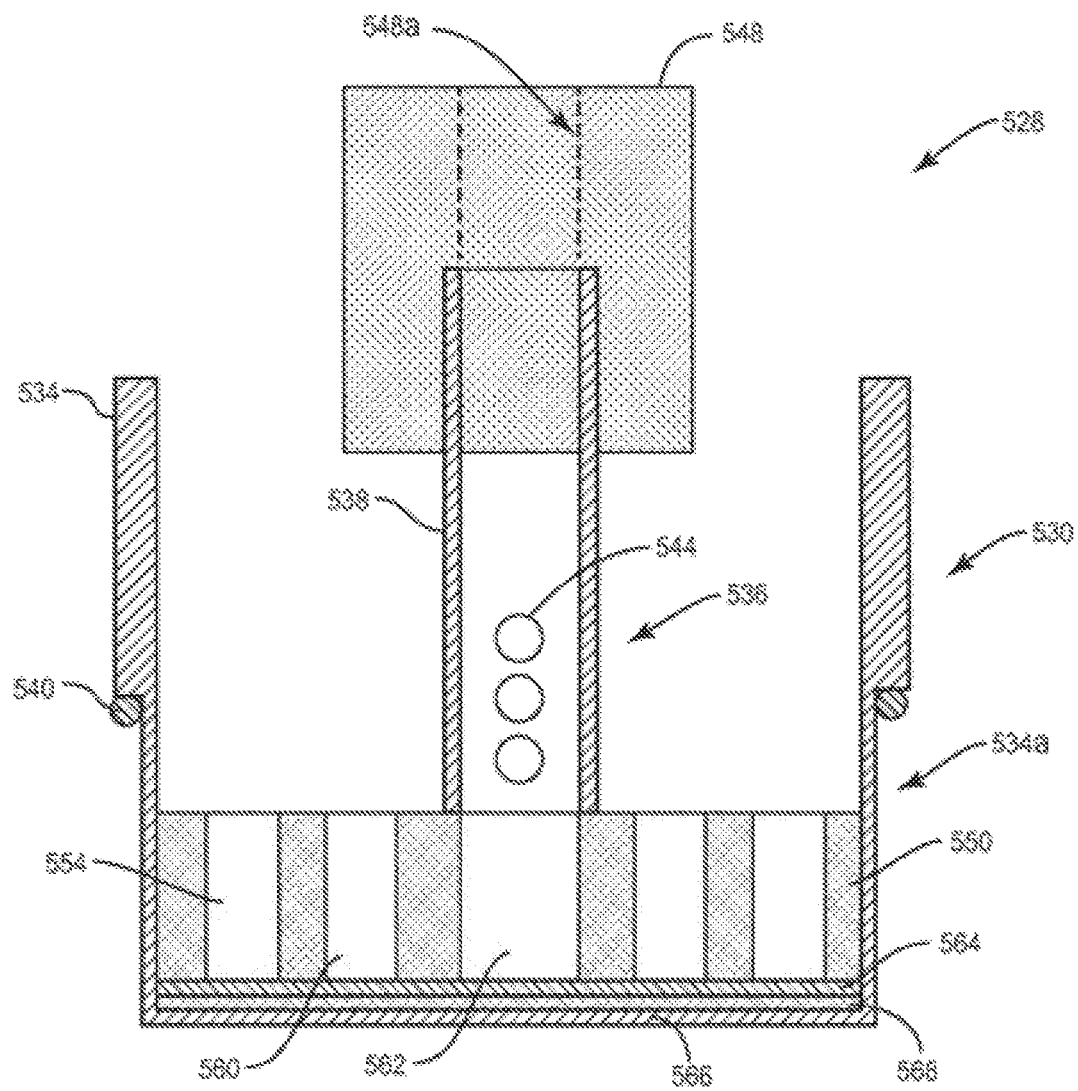

[FIG. 3]
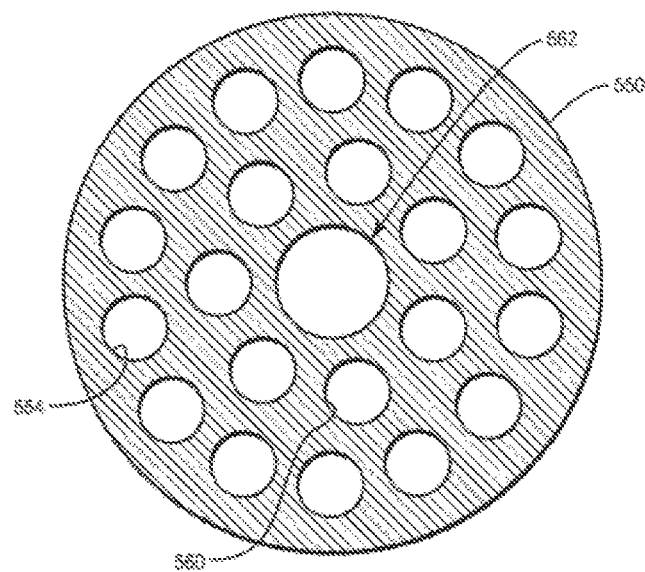

SUPER ABSORBENT RESIN

CROSS-REFERENCE TO RELATED APPLICATIONS

The present application is a national phase entry under 35 U.S.C. § 371 of International Application No. PCT/KR2016/005809 filed Jun. 1, 2016, claims priority from Korean Patent Application Nos. 10-2015-0077534 and 10-2016-0067426, filed on Jun. 1, 2015, and May 31, 2016, respectively, the disclosures of which are hereby incorporated by reference herein.

TECHNICAL FIELD

The present invention relates to a superabsorbent polymer having a remarkably improved anti-rewetting effect.

Background Art

A superabsorbent polymer (SAP) is a synthetic polymeric material capable of absorbing moisture from about 500 to 1000 times its own weight. Various manufacturers have denominated it as different names, such as SAM (Super Absorbency Material), AGM (Absorbent Gel Material), etc. Since such superabsorbent polymers started to be practically applied in sanitary products, now they have been widely used not only for hygiene products such as disposable diapers for children, sanitary napkins, etc., but also for water retaining soil products for gardening, water stop materials for the civil engineering and construction, sheets for raising seedling, fresh-keeping agents for food distribution fields, materials for poultice, etc.

In most cases, these superabsorbent polymers have been widely used in the field of hygienic materials such as diapers, sanitary napkins, etc. For these applications, superabsorbent polymers are required to exhibit high absorbency with respect to moisture, etc., must not release absorbed water even under an external pressure, and also must maintain the shape under volume expansion (swelling) due to water absorption to show excellent permeability.

Reportedly, it is difficult to improve centrifuge retention capacity (CRC), which is a basic physical property of showing water absorption and retention capacities of the superabsorbent polymer, and absorbency under load (AUL), which is a property of retaining absorbed water even under an external pressure, at the same time. The reason is that when the overall crosslinking density of the superabsorbent polymer is controlled to be low, centrifuge retention capacity becomes relatively high, but a crosslinking structure becomes loose and gel strength becomes low, leading to a reduction in absorbency under load. On the contrary, when the crosslinking density is controlled to be high, and therefore absorbency under load is improved, water is hardly absorbed between compact crosslinking structures, leading to a reduction in basic centrifuge retention capacity. Because of the above-described reasons, there have been limitations in proving superabsorbent polymers in which centrifuge retention capacity and absorbency under load are improved at the same time.

However, superabsorbent polymers have been required to have higher absorption performances with recent slimness of sanitary materials such as diapers, sanitary napkins, etc. Of them, simultaneous enhancement of centrifuge retention capacity and absorbency under load which are incompatible physical properties, and improvement of liquid permeability are emerging as important issues.

Further, a pressure by a user's weight may be applied to sanitary materials such as diapers, sanitary napkins, etc. In particular, when liquid is absorbed by the superabsorbent polymer used in sanitary materials such as diapers, sanitary napkins, etc., and then a pressure by a user's weight is applied thereto, a rewetting phenomenon may occur, in which the rewetting phenomenon causes the superabsorbent polymer to release part of the absorbed liquid again. Therefore, to avoid this rewetting phenomenon, many attempts have been made to improve absorbency under load, liquid permeability, etc. However, a specific method capable of effectively avoiding the rewetting phenomenon has not been suggested yet.

DISCLOSURE

Technical Problem

The present invention provides a superabsorbent polymer capable of effectively avoiding a rewetting phenomenon while showing excellent absorption properties.

Technical Solution

An embodiment of the present invention has the following constitution:

(1) a superabsorbent polymer having an average particle size of 300 μm to 600 μm, wherein a gel, which is obtained by swelling 1 g of the superabsorbent polymer in 20 g of 0.9% by weight of a sodium chloride aqueous solution for 10 minutes, has an average particle size of 600 μm to 1000 μm.

(2) the superabsorbent polymer described in (1), wherein a particle having a particle size of 300 μm to 600 μm is 45% by weight to 85% by weight.

(3) the superabsorbent polymer described in (1) or (2), wherein a particle having a particle size of more than 0 μm and 300 μm or less is 15% by weight to 25% by weight.

(4) the superabsorbent polymer described in any one of (1) to (3), wherein a fraction of a gel having a particle size of more than 0 μm and 600 μm or less is 5% by weight to 30% by weight.

(5) the superabsorbent polymer described in any one of (1) to (4), wherein centrifuge retention capacity (CRC) in a physiological saline solution is 28 g/g to 35 g/g, absorbency under load (AUL) of 0.9 psi in the physiological saline solution is 14 g/g to 22 g/g, free swell gel bed permeability (GBP) in the physiological saline solution is 40 darcy to 100 darcy, and a vortex time is 20 seconds to 60 seconds.

Another embodiment of the present invention has the following constitution:

(6) A preparation method including the steps of: performing crosslinking polymerization of a monomer mixture in the presence of an internal crosslinking agent to form a water-containing gel polymer, the monomer mixture including water-soluble ethylene-based unsaturated monomers having acidic groups which are at least partially neutralized, a foaming agent, a foam promoter, and a surfactant; drying, pulverizing, and size-sorting the water-containing gel polymer to form a base polymer powder; and additionally crosslinking the surface of the base polymer powder in the presence of a surface crosslinking agent to form a surface-crosslinked layer.

(7) The preparation method described in (6), wherein one or more selected from the group consisting of magnesium carbonate, calcium carbonate, sodium bicarbonate, sodium carbonate, potassium bicarbonate, and potassium carbonate are used as the foaming agent.

(8) The preparation method described in (6) or (7), wherein polysiloxane with polyether side chains is used as the surfactant.

(9) The preparation method described in any one of (6) to (8), wherein an inorganic acid aluminum salt and/or an organic acid aluminum salt are/is used as the foam promoter.

(10) The preparation method described in any one of (6) to (9), wherein the foaming agent is used in an amount of about 0.05% by weight to about 5.0% by weight with respect to a total weight of the monomer mixture, the foam promoter is used in an amount of about 0.01% by weight to about 3% by weight with respect to the total weight of the monomer mixture, and the surfactant is used in an amount of about 0.001% by weight to about 1% by weight with respect to the total weight of the monomer mixture.

Effect of the Invention

A superabsorbent polymer according to an embodiment of the present invention may exhibit a high absorption rate and high gel strength even in a partially swollen state, because a size of partially swollen gel particles is optimized. Accordingly, the superabsorbent polymer may be used to effectively avoid a rewetting phenomenon.

BRIEF DESCRIPTION OF DRAWINGS

FIGS. 1 to 3 are schematic views of an exemplary apparatus for measuring gel bed permeability and components provided in the apparatus.

DETAILED DESCRIPTION OF THE EMBODIMENTS

Hereinafter, a superabsorbent polymer according to a specific embodiment of the present invention will be described.

According to an embodiment of the present invention, provided is a superabsorbent polymer having an average particle size of 300 μm to 600 μm, wherein a gel, which is obtained by swelling 1 g of the superabsorbent polymer in 20 g of 0.9% by weight of a sodium chloride aqueous solution for 10 minutes, has an average particle size of 600 μm to 1000 μm.

Experimental results of the present inventors confirmed that when the gel, which is obtained by partially swelling the superabsorbent polymer having an average particle size of 300 μm to 600 μm under the above conditions, has an average particle size within a range of 600 μm to 1000 μm, the superabsorbent polymer may have an optimized pore size, porosity, etc. to exhibit a high absorption rate and excellent liquid permeability. It was also confirmed that due to these characteristics, the superabsorbent polymer may exhibit a high absorption rate, excellent absorbency under load, and liquid permeability even in a partially swollen state, thereby effectively avoiding a rewetting phenomenon, in which the rewetting phenomenon causes the liquid absorbed by the superabsorbent polymer to leak back out by an external pressure, thereby completing the present invention.

Accordingly, as long as an average particle size of a gel, which is obtained by partially swelling any kind of superabsorbent polymer under the above-described conditions, satisfies the above-described range, it is possible to provide a superabsorbent polymer, in which the rewetting phenomenon is effectively suppressed.

More specifically, the gel obtained by partially swelling the superabsorbent polymer under the above conditions may have an average particle size of 600 μm to 1000 μm, 650 μm to 950 μm, or 700 μm to 900 μm. This superabsorbent polymer may have an optimized pore size, porosity, etc. to exhibit a high absorption rate and excellent liquid permeability, thereby showing a more excellent anti-rewetting effect.

The average particle size of the gel obtained by partial swelling may be measured from the gel obtained by partially swelling the superabsorbent polymer under the above-described conditions by various methods known in the art to which the present invention pertains.

In detail, 1 g of the superabsorbent polymer is put in a plastic bag, and the superabsorbent polymer is swollen for 10 minutes by adding 20 g of 0.9% by weight of a physiological saline solution thereto, thereby obtaining the gel. The plastic bag is any plastic bag, as long as it is made of a material not absorbing the physiological saline solution. A non-limiting example thereof may be a plastic bag made of PE (polyethylene).

To the gel thus obtained, silica may be added in order to readily measure the average particle size of the gel. Silica may prevent a phenomenon in which the gels stick to each other because of the wet surface thereof during a process of size-sorting the gels. The addition of silica does not change a particle size distribution of the gel, and therefore, any hydrophobic or hydrophilic silica may be used as long as it is able to prevent the sticking phenomenon of the gel during the size-sorting process. Further, the particle size distribution of the gel is not influenced by the addition amount of silica, and therefore, silica may be used in an appropriate amount. For non-limiting example, to obtain the equal particle size distribution with reproducibility, silica may be sufficiently applied to the surface of the gels and the particle sizes of the gels are measured.

The average particle size of the gel may be measured according to various methods known in the art to which the present invention pertains. For example, the average particle size of the gel may be measured according to European Disposables and Nonwovens Association (EDANA) standard WSP 220.2 method.

Meanwhile, the room temperature, as used herein, refers to a natural temperature without heating or cooling, about 1° C. to about 30° C., about 5° C. to about 30° C., or about 15° C. to about 25° C.

As the average particle size of the gel obtained by partial swelling under the above conditions according to an embodiment satisfies the above-described range, the superabsorbent polymer may exhibit a uniform particle size distribution.

For example, the superabsorbent polymer of an embodiment may include a particle having a particle size of 300 μm to 600 μm in an amount of 45% by weight to 85% by weight. Accordingly, the superabsorbent polymer may exhibit a high absorption rate and excellent gel strength even after being partially swollen.

For another example, the superabsorbent polymer of an embodiment may include a particle having a particle size of more than 0 μm and 300 μm or less in an amount of 15% by weight to 25% by weight.

Since the superabsorbent polymer is partially swollen to readily form gels having a uniform particle size distribution, gel particles having a small particle size may be provided from the superabsorbent polymer having a small particle size. Accordingly, the superabsorbent polymer having the particle size distribution may exhibit a more improved anti-rewetting effect.

Further, the superabsorbent polymer may include a particle having a particle size of 300 μm to 600 μm in an amount of 45% by weight to 85% by weight and a particle having a particle size of more than 0 μm and 300 μm or less in an amount of 15% by weight to 25% by weight. In this case, the superabsorbent polymer may include a particle having a particle size of more than 600 μm in a residual amount. The superabsorbent polymer having the above particle size distribution may exhibit more improved absorption rate and gel strength in a partially swollen state.

Further, with regard to the superabsorbent polymer according to an embodiment, a fraction of a gel having a particle size of more than 0 μm and 600 μm or less may be 5% by weight to 30% by weight, or 5% by weight to 20% by weight. The gel is obtained by partially swelling the superabsorbent polymer under the above-described conditions.

This superabsorbent polymer may exhibit higher absorption rate and higher gel strength even in a partially swollen state, due to gel particles having a small particle size. Accordingly, the superabsorbent polymer may exhibit a remarkably improved anti-rewetting effect.

In particular, when the superabsorbent polymer has the above-described particle size distribution, a fraction of the gel having a particle size of more than 0 μm and 600 μm or less may satisfy the above-described range.

Meanwhile, the superabsorbent polymer according to an embodiment, wherein the average particle size of the gel obtained by partially swelling the superabsorbent polymer under the conditions satisfies the above-described range, may have an optimized pore size, porosity, etc. to show excellent absorption performances.

More specifically, the superabsorbent polymer according to an embodiment may exhibit characteristics that centrifuge retention capacity (CRC) in a physiological saline solution is 28 g/g to 35 g/g, 28.5 g/g to 34 g/g, or 29 g/g to 33 g/g, absorbency under load (AUL) of 0.9 psi in the physiological saline solution is 14 g/g to 22 g/g, 15 g/g to 21 g/g, 16 g/g to 20 g/g, or 18 g/g to 20 g/g, free swell gel bed permeability (GBP) in the physiological saline solution is 40 darcy to 100 darcy, 45 darcy to 90 darcy, or 50 darcy to 80 darcy, and a vortex time is 20 seconds to 60 seconds, 25 seconds to 55 seconds, or 30 seconds to 50 seconds.

The superabsorbent polymer having these characteristics according to an embodiment may exhibit not only excellent basic absorption performances but also a remarkably improved anti-rewetting effect, and therefore, it may be applied to a variety of hygiene products such as diapers, etc., thereby exhibiting very excellent overall physical properties.

In particular, when the superabsorbent polymer having these characteristics according to an embodiment includes a particle having a particle size of 300 μm to 600 μm in an amount of 45% by weight to 85% by weight or a particle having a particle size of more than 0 μm and 300 μpm or less in an amount of 15% by weight to 25% by weight, or has a fraction of a gel having a particle size of more than 0 μm and 600 μm or less in an amount of 5% by weight to 30% by weight, or satisfies two or more of these conditions, the superabsorbent polymer may exhibit not only excellent basic absorption performances but also excellent absorption rate and gel strength even in a partially swollen state, thereby exhibiting a remarkably improved anti-rewetting effect and high drying efficiency.

Meanwhile, the centrifuge retention capacity (CRC) in a physiological saline solution may be measured in accordance with EDANA method WSP 241.2. More specifically, the centrifuge retention capacity may be calculated by the following Calculation Formula 1, after size-sorting the superabsorbent polymer to prepare a superabsorbent polymer having a particle size of 300 μm to 600 μm, and allowing the superabsorbent polymer to absorb the physiological saline solution over 30 minutes:

$$CRC(g/g)=\{[W_2(g)-W_1(g)]/W_0(g)\}-1 \quad \text{[Calculation Formula 1]}$$

wherein $W_0(g)$ is an initial weight (g) of the superabsorbent polymer having a particle size of 300 μm to 600 μm, $W_1(g)$ is a weight of an apparatus, which is measured after draining water off at 250 G for 3 minutes using a centrifuge without the superabsorbent polymer, and $W_2(g)$ is the weight of the apparatus including the superabsorbent polymer, which is measured after immersing the superabsorbent polymer having a particle size of 300 μm to 600 μm in 0.9 wt % physiological saline solution at room temperature for 30 minutes and draining water off at 250 G for 3 minutes using a centrifuge.

Further, the absorbency under load (AUL) of 0.9 psi may be measured in accordance with EDANA method WSP 242.2. More specifically, the absorbency under load may be calculated by the following Calculation Formula 2, after allowing the superabsorbent polymer to absorb the physiological saline solution under a load of about 0.9 psi over 1 hour:

$$AUL(g/g)=[W_4(g)-W_3(g)]/W_0(g) \quad \text{[Calculation Formula 2]}$$

wherein $W_0(g)$ is the initial weight (g) of the superabsorbent polymer, $W_3(g)$ is the sum of the weight of the superabsorbent polymer and the weight of the apparatus capable of providing a load for the superabsorbent polymer, and $W_4(g)$ is the sum of the weight of the superabsorbent polymer after allowing the superabsorbent polymer to absorb the physiological saline solution under a load (0.9 psi) for 1 hour and the weight of the apparatus capable of providing a load for the superabsorbent polymer.

$W_0(g)$ described in Calculation Formulae 1 and 2 corresponds to the initial weight before absorbing the physiological saline solution into the superabsorbent polymer, and may be the same as or different from each other.

The gel bed permeability (GBP) in the physiological saline solution may be measured in a unit of Darcy or $cm^2$ in accordance with the following method described in Patent Application No. 2014-7018005. 1 darcy means that a fluid of 1 cp viscosity flows 1 mm per sec through 1 $cm^2$ under a pressure gradient of 1 atm per 1 cm. The gel bed permeability has the same units as area, and 1 darcy is equal to $0.98692 \times 10^{-12}$ $m^2$ or $0.98692 \times 10^{-8}$ $cm^2$.

More specifically, GBP, as used herein, means a degree of penetration (or permeability) of a swollen gel layer (or bed) under what is commonly referred to as a free swell state of 0 psi (Gel Bed Permeability (GBP) Under 0 psi Swell Pressure Test), and may be measured by using an apparatus shown in FIGS. 1 to 3.

Referring to FIGS. 1 to 3, in an apparatus 500 for measuring GBP, a test apparatus assembly 528 includes a sample container 530 and a plunger 536. The plunger includes a shaft 538 having a cylinder hole bored down the longitudinal axis and a head 550 positioned at the bottom of the shaft. The shaft hole 562 has a diameter of about 16 mm. The plunger head is attached to the shaft, for example, by an adhesive. Twelve holes 544 are bored into the radial axis of the shaft, three positioned at every 90 degrees having diameters of about 6.4 mm. The shaft 538 is machined from a LEXAN rod or equivalent material and has an outer diameter of about 2.2 cm and an inner diameter of about 16 mm. The plunger head 550 has a concentric inner ring of seven holes 560 and an outer ring of 14 holes 554, all holes having a diameter of about 8.8 mm as well as a hole of about 16 mm aligned with the shaft. The plunger head 550 is machined from a LEXAN rod or equivalent material and has a height of about 16 mm and a diameter sized such that it fits within the cylinder 534 with minimum wall clearance but still slides freely. The total length of the plunger head 550 and shaft 538 is about 8.25 cm, but may be machined at the top of the shaft to obtain the desired mass of the plunger 536. The plunger 536 includes a 100 mesh stainless steel cloth screen 564 that is biaxially stretched to tautness and attached to the lower end of the plunger 536. The screen is attached to the plunger head 550 using an appropriate solvent that causes the screen to be securely adhered to the plunger head 550. Care must be taken to avoid excess solvent migrating into the open portions of the screen and reducing the open area for liquid flow. Acrylic solvent Weld-on 4 from IPS Corporation (having a place of business in Gardena, Calif., USA) may be suitably used. The sample container 530 includes a cylinder 534 and a 400 mesh stainless steel cloth screen 566 that is biaxially stretched to tautness and attached to the lower end of the cylinder 534. The screen is attached to the cylinder using an appropriate solvent that causes the screen to be securely adhered to the cylinder. Care must be taken to avoid excess solvent migrating into the open portions of the screen and reducing the open area for liquid flow. Acrylic solvent Weld-on 4 from IPS Corporation (having a place of business in Gardena, Calif., USA) may be suitably used. A gel particle sample (swollen superabsorbent polymer), indicated as 568 in FIG. 2, is supported on the screen 566 within the cylinder 534 during testing.

The cylinder 534 may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm and a height of about 7.95 cm. A step is machined into the outer diameter of the cylinder 534 such that a region 534a with an outer diameter of 66 mm exists for the bottom 31 mm of the cylinder 534. An o-ring 540 which fits the diameter of region 534a may be placed at the top of the step.

An annular weight 548 has a counter-bored hole about 2.2 cm in diameter and 1.3 cm deep so that it slips freely onto the shaft 538. The annular weight also has a thru-bore 548a of about 16 mm. The annular weight 548 may be made from stainless steel or from other suitable materials resistant to corrosion by 0.9% by weight of a physiological saline solution (sodium chloride aqueous solution). The combined weight of the plunger 536 and annular weight 548 equals about 596 g, which corresponds to a pressure applied to the sample 568 of about 0.3 psi, or about 20.7 dynes/cm$^2$ (2.07 kPa), over a sample area of about 28.27 cm$^2$.

When a test solution flows through the test apparatus during GBP testing, the sample container 530 generally rests on a weir 600. The purpose of the weir is to divert liquid that overflows the top of the sample container 530 and diverts the overflow liquid to a separate collection device 601. The weir may be positioned above a scale 602 with a beaker 603 resting on it to collect a physiological saline solution passing through the swollen sample 568.

To conduct the gel bed permeability test under "free swell" conditions, the plunger 536, with the weight 548 seated thereon, is placed in an empty sample container 530 and the height from the top of the weight 548 to the bottom of the sample container 530 is measured using a suitable gauge accurate to 0.01 mm. The force the thickness gauge applies during measurement should be as low as possible, preferably less than about 0.74 N. It is important to measure each empty sample container 530 and to keep track of which plunger 536 and weight 548 are used when using a multiple test apparatus.

Further, it is desirable that a base on which the sample container 530 is placed is level, and the top surface of the weight 548 is parallel to the bottom surface of the sample container 530. A test sample is prepared from a superabsorbent polymer to be tested for GBP. For example, a superabsorbent polymer having a particle size of about 300 μm to about 600 μm, which is prescreened through a US standard 30 mesh screen and retained on a US standard 50 mesh screen, is prepared as the test sample. About 2.0 g of the sample is placed in the sample container 530 and spread out evenly on the bottom of the sample container. The container, with 2.0 g of sample in it, without the plunger 536 and weight 548 therein, is then submerged in the 0.9% by weight of a physiological saline solution for about 60 minutes to allow the sample to swell free of any restraining load. At this time, the sample container 530 is set on a mesh located in a liquid reservoir so that the sample container 530 is raised slightly above the bottom of the liquid reservoir. The mesh does not inhibit the flow of the physiological saline solution into the sample container 530. A suitable mesh may be obtained as part number 7308 from Eagle Supply and Plastic (having a place of business in Appleton, Wis., USA). During saturation, a depth of the physiological saline solution may be controlled such that the surface within the sample container is defined solely by the sample, rather than the physiological saline solution.

At the end of this period, the plunger 536 and weight 548 assembly is placed on the saturated sample 568 in the sample container 530 and then the sample container 530, plunger 536, weight 548, and sample 568 are removed from the solution. Then, before GBP measurement, the sample container 530, plunger 536, weight 548, and sample 568 are to remain at rest for about 30 seconds on a large grid nondeformable plate of uniform thickness. The plate will prevent liquid in the sample container from being released onto a flat surface due to surface tension. The plate has an overall dimension of 7.6 cm×7.6 cm, and each grid has a size dimension of 1.59 cm long×1.59 cm wide×1.12 cm deep. A material suitable for the plate is a parabolic diffuser panel, catalogue number 1624K27, available from McMaster Carr Supply Company (having a place of business in Chicago, Ill., USA), which may then be cut to the proper dimensions.

The height from the bottom of the weight 548 to the top of the sample container 530 is measured again by using the same thickness gauge used previously, provided that the zero point is unchanged from the initial height measurement. The height measurement should be made as soon as practicable after the thickness gauge is engaged. The height measurement of the empty assembly where the plunger 536 and the weight 548 are placed in the empty sample container 530 is subtracted from the height measurement obtained after saturating the sample 568. The resulting value is the thickness or height "H" of the saturated sample 568. Further, if the plate is contained in the assembly containing the saturated sample 568, this plate must also be present when measuring the height of the empty assembly.

The GBP measurement is initiated by delivering a flow of 0.9% physiological saline solution into the sample container 530 with the saturated sample 568, plunger 536, and weight

548 inside. The flow rate of the physiological saline solution into the container is adjusted to cause the physiological saline solution to overflow the top of the cylinder 534, resulting in a consistent head pressure equal to the height of the sample container 530. The physiological saline solution may be added by any suitable means that is sufficient to ensure a small, but consistent amount of overflow from the top of the cylinder, such as with a metering pump 604. The overflow liquid is diverted into a separate collection device 601. The quantity of solution passing through the sample 568 versus time is measured gravimetrically using a scale 602 and a beaker 603. Data points from the scale 602 are collected every second for at least 60 seconds once the overflow has begun. Data collection may be taken manually or with data collection software. The flow rate, Q through the swollen sample 568 is determined in units of g/sec by a linear least-square fit of fluid (g) passing through the sample 568 versus time (sec).

GBP ($cm^2$) may be calculated from the obtained data according to the following Calculation Formula 3 to confirm gel bed permeability:

$$K=[Q*H*\mu]/[A*\rho*P] \quad \text{[Calculation Formula 3]}$$

where K is gel bed permeability ($cm^2$),
Q is a flow rate (g/sec),
H is a height of swollen sample (cm),
$\mu$ is liquid viscosity (p) (viscosity of the test solution to be used in this test is about 1 cp),
A is a cross-sectional area for liquid flow (28.27 $cm^2$ for the sample container used in this test),
$\rho$ is a liquid density ($g/cm^3$) (about 1 $g/cm^3$ for the test solution used in this test), and
P is a hydrostatic pressure (dynes/$cm^2$) (normally about 7,797 dynes/$cm^2$).

The hydrostatic pressure is calculated from $P=\rho*g*h$, wherein $\rho$ is a liquid density ($g/cm^3$), g is gravitational acceleration (nominally 981 cm/$sec^2$), and h is a fluid height (e.g., 7.95 cm for the GBP test described herein).

Meanwhile, the vortex time may be measured in seconds in accordance with a method described in International Patent Application No. 1987-003208. More specifically, the vortex time may be calculated by measuring a time which is required until the vortex disappears, after adding 2 g of the superabsorbent polymer to 50 mL of a physiological saline solution and then agitating it at 600 rpm.

The superabsorbent polymer of an embodiment, wherein the average particle size of the gel obtained by partial swelling under the above conditions is within the above range, may be provided by properly controlling the structures or physical properties of various different kinds of superabsorbent polymers known in the art to which the present invention pertains. More specifically, like the previous existing superabsorbent polymers, the superabsorbent polymer of an embodiment may basically include a crosslinked polymer as a base polymer powder, wherein the crosslinked polymer is obtained from crosslinking polymerization of water-soluble ethylene-based unsaturated monomers, and may include a surface-crosslinked layer formed on the base polymer powder. In addition, the superabsorbent polymer of an embodiment may include a structure or additional component such that the gel obtained by partial swelling under the above conditions has an average particle size within the above range.

For example, the superabsorbent polymer of an embodiment may have an increased absorption area, as compared to the existing superabsorbent polymer, and therefore, the gel obtained by partial swelling under the above conditions may have an average particle size within the above range. Specifically, a foaming agent capable of generating bubbles, a foam promoter for promoting bubble generation, and a surfactant for stable bubble formation may be used during polymerization of the base polymer powder, thereby providing the superabsorbent polymer, in which the gel obtained by partial swelling under the above conditions has an average particle size within the above range.

More specifically, the superabsorbent polymer of an embodiment may be prepared by a preparation method including the steps of: performing crosslinking polymerization of a monomer mixture in the presence of an internal crosslinking agent to form a water-containing gel polymer, the monomer mixture including water-soluble ethylene-based unsaturated monomers having acidic groups which are at least partially neutralized, a foaming agent, a foam promoter, and a surfactant; drying, pulverizing, and size-sorting the water-containing gel polymer to form a base polymer powder; and additionally crosslinking the surface of the base polymer powder in the presence of a surface crosslinking agent to form a surface-crosslinked layer.

In the preparation method, as the water-soluble ethylene-based unsaturated monomer, one or more selected from the group consisting of an anionic monomer such as acrylic acid, (meth)acrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, and salts thereof; a nonionic hydrophilic monomer such as (meth)acrylamide, N-substituted (meth)acrylate, 2-hydroxyethyl(meth)acrylate, 2-hydroxypropyl (meth)acrylate, methoxy polyethylene glycol (meth)acrylate, or polyethylene glycol (meth)acrylate; and an amino group-containing unsaturated monomer such as (N,N)-dimethylaminoethyl(meth)acrylate or (N,N)-dimethylaminopropyl(meth)acrylamide, and a quaternary compound thereof may be used. Among them, acrylic acid or salts thereof, for example, acrylic acid which is at least partially neutralized, and/or alkali metal salts thereof such as sodium salts thereof may be used, and it is possible to prepare a superabsorbent polymer having superior physical properties by using these monomers. When the alkali metal salt of acrylic acid is used as the monomer, acrylic acid may be used after being neutralized with a basic compound such as caustic soda (NaOH). In this regard, a neutralization degree of the water-soluble ethylene-based unsaturated monomer may be controlled in the range of about 50% to about 95% or about 70% to about 85%. When the water-soluble ethylene-based unsaturated monomer is neutralized within the above range, it is possible to provide a superabsorbent polymer having excellent centrifuge retention capacity without concern about precipitation.

In the monomer mixture including the water-soluble ethylene-based unsaturated monomers, the concentration of the water-soluble ethylene-based unsaturated monomer may be about 20% by weight to about 60% by weight, or about 40% by weight to about 50% by weight, based on a total weight of the monomer mixture including raw materials described below and a solvent, and the concentration may be properly controlled, in consideration of a polymerization time and reaction conditions. However, if the monomer concentration is too low, the yield of the superabsorbent polymer may become low and an economic problem may occur. On the contrary, if the concentration is too high, there is a process problem that a part of the monomers is precipitated, or pulverization efficiency is lowered upon pulverization of the polymerized water-containing gel polymer, and the physical properties of the superabsorbent polymer may be deteriorated.

As the foaming agent used to form a plurality of pores in the base polymer powder, carbonate of which bubble formation may be promoted by the foam promoter and which enables stable bubble formation by the surfactant may be used.

More specific examples of the carbonate may include one or more selected from the group consisting of magnesium carbonate, calcium carbonate, sodium bicarbonate, sodium carbonate, potassium bicarbonate, and potassium carbonate.

As the foam promoter for promoting bubble generation of the foaming agent, an inorganic acid aluminium salt such as aluminum sulfate, aluminum chloride, etc., or an organic acid aluminium salt such as aluminum lactate, aluminum oxalate, aluminum citrate, aluminum urate, etc. may be used.

If the water-containing gel polymer is formed by using only the foaming agent and the surfactant without the foam promoter, an optimized porosity and pore structure may not be achieved, and thus the average particle size of the gel partially swollen under the above conditions according to an embodiment becomes out of the above range.

As the surfactant for inducing stable bubble formation by the foaming agent and the foam promoter, silicone-based surfactants may be used. These silicone-based surfactants may greatly contribute to providing a superabsorbent polymer which has appropriate porosity to exhibit excellent centrifugal retention capacity and absorbency under load, and also has an appropriate density to be easy to handle during processing such as size-sorting, etc.

As the silicone-based surfactants, polysiloxane containing polyether side chains, etc. may be used. Among them, a silicone-based surfactant having a structure of a polydimethylsiloxane backbone with polyether sides chains such as poly(ethylene oxide) or poly(propylene oxide) may be used. Examples of the surfactant may include OFX-0190 Fluid (PEG/PPG-18/18 Dimethicone), OFX-0193 Fluid (PEG-12 Dimethicone), OFX-5220 Fluid (PEG/PPG-17/18 Dimethicone), OFX-5324 Fluid (PEG-12 Dimethicone) of Xiameter (R), etc.

In the monomer mixture including the water-soluble ethylene-based unsaturated monomers, etc., a concentration of the foaming agent may be about 0.05% by weight to about 5.0% by weight, or about 0.1% by weight to about 3% by weight with respect to the total monomer mixture, a concentration of the foam promoter may be about 0.01% by weight to about 3% by weight or about 0.5% by weight to about 2% by weight with respect to the total monomer mixture, and a concentration of the surfactant may be about 0.001% by weight to about 1% by weight, or about 0.01% by weight to about 0.5% by weight with respect to the total monomer mixture.

When the foaming agent, the foam promoter, and the surfactant may be used within the above ranges, the pore size, porosity, etc. of the superabsorbent polymer may be optimized to remarkably improve the absorption surface area, thereby improving the absorption rate and anti-rewetting effect.

Meanwhile, in order to allow the water-containing gel polymer to contain a large amount of bubbles generated by the foaming agent, foam promoter, and surfactant, and to stably maintain a plurality of pores contained in the water-containing gel polymer in the subsequent process, a hydroxyl group-containing compound may be used in the step of forming the water-containing gel polymer.

More specifically, when the hydroxyl group-containing compound is used in the step of forming the water-containing gel polymer, viscosity of a polymerization solution may be improved to shorten a gelation time at the time of performing crosslinking polymerization of the monomer mixture including the water-soluble ethylene-based unsaturated monomers, etc. Therefore, escaping of a large amount of bubbles generated by the foaming agent, etc. from the polymerization solution may be effectively prevented, and a large amount of bubbles may be included in the water-containing gel polymer. Further, the hydroxyl group-containing compound may be included in a superabsorbent polymer finally prepared to improve wettability of the superabsorbent polymer. Accordingly, the superabsorbent polymer may have more improved absorption rate under no pressure or under a pressure.

Polyvinyl alcohol or polyalkylene glycol such as polyethylene glycol may be used as the hydroxyl group-containing compound. A concentration of the hydroxyl group-containing compound may be about 0.1% by weight to about 1% by weight with respect to the total monomer mixture. Within this range, the absorption area and wettability of the superabsorbent polymer may be effectively increased.

As the internal crosslinking agent to introduce a basic crosslinked structure into the base polymer powder, any internal crosslinking agent having a crosslinkable functional group which has been generally used in the preparation of the superabsorbent polymer may be used without limitation. However, to further improve physical properties of the superabsorbent polymer by introducing a proper crosslinked structure into the base polymer powder, a multifunctional acrylate-based compound having a plurality of ethylene oxide groups may be used as the internal crosslinking agent. More specific examples of the internal crosslinking agent may include one or more selected from the group consisting of polyethylene glycol diacrylate (PEGDA), glycerin diacrylate, glycerin triacrylate, non-modified or ethoxylated trimethylol propane triacrylate (TMPTA), hexanediol diacrylate, and triethylene glycol diacrylate. The internal crosslinking agent may be included in an amount of about 0.01% by weight to about 0.5% by weight with respect to the monomer mixture, thereby crosslinking the polymerized polymer.

In addition, the monomer mixture may further include a polymerization initiator which is generally used in the preparation of the superabsorbent polymer.

Specifically, the polymerization initiator may be a thermal polymerization initiator or a photo-polymerization initiator by UV irradiation, depending on a polymerization method. However, even though the photo-polymerization is performed, a certain amount of heat may be generated by UV irradiation or the like, and also generated with exothermic polymerization reaction. Therefore, the thermal polymerization initiator may be further included.

As the photo-polymerization initiator, a compound capable of forming radicals by a light such as UV may be used without limitations in the constitution.

For example, one or more selected from the group consisting of benzoin ether, dialkyl acetophenone, hydroxyl alkylketone, phenyl glyoxylate, benzyl dimethyl ketal, acyl phosphine, and α-aminoketone may be used as the photo-polymerization initiator. Meanwhile, as the specific example of acyl phosphine, commercial lucirin TPO, namely, 2,4,6-trimethyl-benzoyl-trimethyl phosphine oxide may be used. More various photo-polymerization initiators are well disclosed in "UV Coatings: Basics, Recent Developments and New Application (Elsevier, 2007)" written by Reinhold Schwalm, p115, however, they are not limited to the above described examples.

The photo-polymerization initiator may be included in an amount of about 0.01% by weight to about 1.0% by weight with respect to the monomer mixture. If the concentration of the photo-polymerization initiator is too low, the polymerization rate may become low. If the concentration of the photo-polymerization initiator is too high, a molecular weight of the superabsorbent polymer may become low and its physical properties may not be uniform.

Further, one or more selected from the group consisting of persulfate-based initiators, azo-based initiators, hydrogen peroxide, and ascorbic acid may be used as the thermal polymerization initiator. Specific examples of the persulfate-based initiators may include sodium persulfate ($Na_2S_2O_8$), potassium persulfate ($K_2S_2O_8$), ammonium persulfate (($NH_4)_2S_2O_8$), etc. Examples of the azo-based initiators may include 2,2-azobis(2-amidinopropane)dihydrochloride, 2,2-azobis-(N,N-dimethylene)isobutyramidine dihydrochloride, 2-(carbamoylazo)isobutylonitrile, 2,2-azobis(2-[2-imidazolin-2-yl]propane)dihydrochloride, 4,4-azobis-(4-cyanovaleric acid), etc. More various thermal polymerization initiators are well-disclosed in 'Principle of Polymerization (Wiley, 1981)' written by Odian, p 203, however, they are not limited to the above described examples.

The thermal polymerization initiator may be included in an amount of about 0.001% by weight to about 0.5% by weight with respect to the monomer mixture. If the concentration of the thermal polymerization initiator is too low, additional thermal polymerization hardly occurs, and thus the addition effect of the thermal polymerization initiator may not be sufficiently obtained. If the concentration of the thermal polymerization initiator is too high, the molecular weight of the superabsorbent polymer may become low and its physical properties may not be uniform.

The monomer mixture may further include an additive such as a thickener, a plasticizer, a preservation stabilizer, an antioxidant, etc., if necessary.

The raw materials such as the above-described water-soluble ethylene-based unsaturated monomer, foaming agent, foam promoter, surfactant, photo-polymerization initiator, thermal polymerization initiator, internal crosslinking agent, and additive may be prepared in the form of a monomer mixed solution being dissolved in a solvent.

In this regard, as the solvent, any solvent may be used without limitations in the constitution as long as it is able to dissolve the above ingredients, and for example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, and N,N-dimethylacetamide may be used in combination.

The solvent may be included in a remaining amount excluding the above described components from the total weight of the monomer mixture.

Meanwhile, the method of forming the water-containing gel polymer by thermal polymerization or photo-polymerization of the monomer mixture may be carried out in a reactor like a kneader equipped with agitating spindles in order to promote bubble generation.

As described above, the water-containing gel polymer which is discharged from the outlet of a reactor by providing a polymerization energy source such as heat or light to the reactor like a kneader equipped with the agitating spindles may have a size of centimeters or millimeters, according to the type of agitating spindles equipped in the reactor. Specifically, the water-containing gel polymer may be obtained in various forms according to the concentration of the monomer mixture fed thereto, the feeding speed, etc. Generally, the water-containing gel polymer having a weight average particle size of about 2 mm to about 50 mm may be obtained.

In this regard, the water-containing gel polymer thus obtained by the method may have generally a water content of about 40% by weight to about 80% by weight. Meanwhile, the term "water content", as used herein, means a water content in the total weight of the water-containing gel polymer, which is obtained by subtracting the weight of the dry polymer from the weight of the water-containing gel polymer. Specifically, the water content is defined as a value calculated by measuring the weight loss according to evaporation of water in the polymer during the drying process of increasing the temperature of the polymer with infrared heating. In this regard, the water content is measured under the drying conditions which are determined as follows; the temperature is increased from room temperature to about 180° C. and then the temperature is maintained at 180° C., and the total drying time is determined as 20 minutes, including 5 minutes for the temperature rising step.

After crosslinking polymerization of the monomers, drying, pulverizing, and size-sorting processes may be performed to obtain the base polymer powder. Through the pulverizing and size-sorting processes, the base polymer powder and the superabsorbent polymer obtained therefrom are suitably prepared and provided such that they have a particle size of about 150 µm to about 850 µm. More specifically, at least about 95% by weight of the base polymer powder and the superabsorbent polymer obtained therefrom may have a particle size of about 150 µm to about 850 µm, and fine powder having a particle size of less than about 150 µm may be less than about 3% by weight.

As such, when particle size distributions of the base polymer powder and the superabsorbent polymer are controlled within the preferred range, the superabsorbent polymer finally prepared may exhibit excellent absorption properties.

Meanwhile, the methods of performing the drying, pulverizing, and size-sorting will be described in more detail as follows.

First, in drying the water-containing gel polymer, a coarse pulverization process may be further carried out before drying in order to increase the efficiency of the drying process, if necessary.

There is no limitation in the constitution of a milling machine to be used. Specifically, any one device selected from the group consisting of a vertical pulverizer, a turbo cutter, a turbo grinder, a rotary cutter mill, a cutter mill, a disc mill, a shred crusher, a crusher, a chopper, and a disc cutter may be used, but it is not limited thereto.

In this regard, the coarse pulverization may be carried out such that the water-containing gel polymer has a particle size of about 2 mm to about 10 mm Due to the high water content, it is technically not easy to pulverize the water-containing gel polymer into a particle size of less than 2 mm, and a phenomenon of agglomeration between the pulverized particles may occur. Meanwhile, when the particle size is larger than 10 mm, the effect of increasing the efficiency of the subsequent drying process may be unsatisfactory.

The water-containing gel polymer coarsely pulverized as above or the water-containing gel polymer immediately after polymerization without the coarse pulverizing step is subjected to drying. In this case, a drying temperature of the drying step may be about 50° C. to about 250° C.

When the drying temperature is lower than 50° C., it is likely that the drying time becomes too long or the physical properties of the superabsorbent polymer finally formed are deteriorated, and when the drying temperature is higher than 250° C., only the surface of the polymer is dried, and thus it is likely that fine powder is generated during the subsequent pulverizing step and the physical properties of the superabsorbent polymer finally formed are deteriorated.

Meanwhile, the drying time may be about 20 minutes or about 15 hours, in consideration of process efficiency, etc., but is not limited thereto.

The drying method of the drying step may also be selected and used without any limitation in the constitution, as long as it is a method generally used for drying the water-containing gel polymer. Specifically, the drying step may be carried out by a method such as hot air supply, infrared irradiation, microwave irradiation, or ultraviolet irradiation. When the drying step as above is finished, the water content of the polymer may be about 0.1% by weight to about 10% by weight.

Subsequently, the dried polymer obtained through the drying step is subjected to a pulverization step.

The polymer powder obtained through the pulverizing step may have a particle size of about 150 μm to about 850 μm. Specific examples of a milling machine used to achieve the above particle size may include a pin mill, a hammer mill, a screw mill, a roll mill, a disc mill, a jog mill, etc., but is not limited thereto.

Also, in order to manage the physical properties of the superabsorbent polymer powder finally commercialized after the pulverization step, a separate process of sorting the polymer powder obtained after the pulverization depending on the particle size may be performed. Preferably, a polymer having a particle size of about 150 μm to about 850 μm is sorted, and only the polymer powder having such a particle size is subjected to the surface crosslinking reaction and finally commercialized. A particle size distribution of the base polymer powder obtained through this process has been described, and a specific description thereof will be omitted.

Meanwhile, after the process of forming the above-described base polymer powder, the surface of the base polymer powder may be further crosslinked in the presence of the surface crosslinking agent to form the surface-crosslinked layer, thereby preparing the superabsorbent polymer.

The surface-crosslinked layer may be formed by using a surface crosslinking agent which has been used in the preparation of the superabsorbent polymer. As the surface crosslinking agent, any surface crosslinking agent known in the art to which the present invention pertains may be used without limitation. More specific examples thereof may include one or more selected from the group consisting of ethylene glycol, propylene glycol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol, glycerol, ethylene carbonate, and propylene carbonate. Such surface crosslinking agent may be used in an amount of about 0.01% by weight to 3% by weight with respect to the total weight of the base polymer powder.

In the surface crosslinking process, the surface crosslinking process may be carried out by further adding one or more inorganic materials selected from the group consisting of silica, clay, alumina, a silica-alumina composite, titania, zinc oxide, and aluminum sulfate, in addition to the surface crosslinking agent. These inorganic materials may be used in a powdery form or in a liquid form, and in particular, alumina powder, silica-alumina powder, titania powder, or a nanosilica solution may be used. Further, the inorganic material may be used in an amount of about 0.05% by weight to about 2% by weight with respect to the total weight of the base polymer powder.

Further, in the surface crosslinking process, when the surface crosslinking is performed by adding a multivalent metal cation instead of the inorganic material or together with the inorganic material, the surface crosslinked structure of the superabsorbent polymer may be further optimized. This may be because the metal cation forms a chelate with a carboxyl group (COOH) of the superabsorbent polymer to further reduce a crosslinking distance.

There is no limitation in the method of adding the surface crosslinking agent, if necessary, the inorganic material and/or the multivalent metal cation to the base polymer powder. For example, a method of adding and mixing the surface crosslinking agent with the base polymer powder in a reactor, a method of spraying the surface crosslinking agent onto the base polymer powder, and a method of continuously mixing the base polymer powder and the surface crosslinking agent while providing them to a mixer that is continuously operated may be used.

When the surface crosslinking agent is added thereto, water and methanol may be further mixed therewith. When water and methanol are added thereto, there is an advantage that the surface crosslinking agent may be evenly dispersed in the base polymer powder. At this time, amounts of water and methanol to be added may be regulated for the purposes of inducing a uniform dispersion of the surface crosslinking agent, preventing an agglomeration phenomenon of the base polymer powder, and optimizing a surface penetration depth of the surface crosslinking agent.

The surface crosslinking reaction may be carried out by heating the base polymer powder, to which the surface crosslinking agent is applied, at about 100° C. or higher for about 20 minutes or more. Particularly, in order to prepare the superabsorbent polymer that may more appropriately satisfy the physical properties according to an embodiment, the surface crosslinking process conditions may be controlled such that a maximum reaction temperature is about 100° C. to about 250° C. The maximum reaction temperature may be maintained for about 20 minutes or more, or for about 20 minutes and 1 hour or less. Furthermore, the heat-up time from the reaction initiation temperature, for example, about 100° C. or higher, to the maximum reaction temperature may be controlled to be about 10 minutes or more, or about 10 minutes or more and 1 hour or less.

A means for raising the temperature for surface crosslinking reaction is not particularly limited. Heating may be performed by providing a heating medium or by directly providing a heat source. In this regard, the type of the heating medium applicable may be a hot fluid such as steam, hot air, hot oil, etc., but is not limited thereto. The temperature of the heating medium provided may be properly selected in consideration of the means of the heating medium, a heating speed, and a target temperature of heating. Meanwhile, an electric heater or a gas heater may be used as the heat source provided directly, but the heat source is not limited to these examples.

The superabsorbent polymer obtained by the above-described preparation method may be partially swollen under the above-described conditions to easily form a gel having a uniform particle size distribution, and therefore, the partially swollen gel may have an average particle size within the above-described range. That is, the superabsorbent polymer obtained by the above-described preparation method may exhibit an excellent absorption rate and high gel strength even in a partially swollen state, since its pore size, porosity, etc. is optimized due to use of the foaming agent, foam promoter, and surfactant. Accordingly, a rewetting phenomenon may be effectively prevented.

Hereinafter, the actions and effects of the present invention will be described in more detail with reference to specific Examples of the present invention. However, these Examples are for illustrative purposes only, and the scope of the invention is not intended to be limited thereby.

EXAMPLE 1

Preparation of Superabsorbent Polymer 11 g (110 ppm with respect to a monomer composition) of 0.5% IRGACURE 819 initiator diluted with acrylic acid and 26 g of 5% polyethyleneglycol diacrylate (PEGDA, a molecular weight of 400) diluted with acrylic acid were mixed to prepare a solution (solution A).

5% trimethylolpropane triacrylate containing 9 mol % of ethylene oxide (Ethoxylated-TMPTA, TMP(EO)9TA, M-3190 Miwon Specialty Chemical Co., Ltd.) diluted with acrylic acid was prepared as a solution B.

Into a 2 L-volume glass reactor surrounded by a jacket in which a heating medium pre-cooled to 25° C. was circulated, 37 g of the solution A and 14 g of the solution B were injected. To the glass reactor, 2.8 g of 1% OFX-0193 (XIAMETER(R)) solution diluted with acrylic acid as a surfactant was injected and mixed, and then 800 g of a 24% caustic soda solution (solution C) was slowly added dropwise and mixed. After confirming that the temperature of the mixed solution increased to about 72° C. or higher by neutralization heat upon adding dropwise the solution C, the mixed solution was left until it was cooled. A neutralization degree of acrylic acid in the mixed solution thus obtained was about 70 mol %.

Meanwhile, a 5% sodium bicarbonate solution diluted with water was prepared as a solution D, and 1.6 g of aluminium sulfate was dissolved in 28 g of 4% sodium persulfate solution diluted with water to prepare a solution E-1.

When the temperature of the mixed solution was cooled to about 45° C., 34 g of the previously prepared solution D was added to the mixed solution and mixed, and the solution E-1 was added thereto at the same time.

Subsequently, the above-prepared mixed solution was poured in a Vat-type tray (15 cm in width×15 cm in length) installed in a square polymerizer which had a light irradiation device installed at the top and was preheated to 80° C., and the mixed solution was subjected to light irradiation. It was confirmed that at about 25 seconds after light irradiation, gel was generated from the surface, and at about 30 seconds after light irradiation, foam generation and polymerization occurred at the same time. Then, the reaction was allowed for additional 2 minutes, and the polymerized sheet was taken and cut in a size of 3 cm×3 cm, and then subjected to a chopping process using a meat chopper to prepare the cut sheet as crumbs.

Subsequently, the crumbs were dried in an oven capable of shifting airflow up and down. The crumbs were uniformly dried by flowing hot air at 180° C. from the bottom to the top for 15 minutes and from the top to the bottom for 15 minutes such that the dried crumbs had a water content of about 2% or less.

The dried crumbs were pulverized using a pulverizer and sorted by size, and a base polymer having a size of about 150 μm to about 850 μm was obtained. Centrifuge retention capacity of the base polymer thus obtained was 36.5 g/g, and a content of the water-soluble component was 14.2% by weight. The centrifuge retention capacity was measured according to EDANA method WSP 241.2, and the content of the water-soluble component was measured according to EDANA method WSP 270.2.

Thereafter, 100 g of the base polymer was mixed with a crosslinking agent solution which was prepared by mixing 3 g of water, 3 g of methanol, 0.4 g of ethylene carbonate, and 0.5 g of Aerosil 200 (EVONIK), and then surface crosslinking reaction was allowed at 190° C. for 30 minutes. The resulting product was pulverized and passed through a sieve to obtain a surface-crosslinked superabsorbent polymer having a particle size of 150 μm to 850 μm.

EXAMPLE 2

Preparation of Superabsorbent Polymer

A base polymer was prepared in the same manner as in Example 1, except that 15 g of the solution D was used instead of 34 g in Example 1. Centrifuge retention capacity of the prepared base polymer was 35.2 g/g and a content of the water-soluble component was 13.9% by weight. The prepared base polymer was used to obtain a surface-crosslinked superabsorbent polymer having a particle size of 150 μm to 850 μm in the same manner as in Example 1.

EXAMPLE 3

Preparation of Superabsorbent Polymer 0.1 g of Aerosil 200 (EVONIK) was added to 100 g of the surface-crosslinked superabsorbent polymer prepared in Example 1, and then subjected to dry mixing to obtain a superabsorbent polymer.

EXAMPLE 4

Preparation of Superabsorbent Polymer

A base polymer was prepared in the same manner as in Example 1, except that a solution (solution E-2) prepared by dissolving 0.8 g of aluminum sulfate in 28 g of 4% sodium persulfate solution diluted with water was used instead of the solution E-1 in Example 1. Centrifuge retention capacity of the prepared base polymer was 37.4 g/g and a content of the water-soluble component was 15.1% by weight. The prepared base polymer was used to obtain a surface-crosslinked superabsorbent polymer having a particle size of 150 μm to 850 μm in the same manner as in Example 1.

EXAMPLE 5

Preparation of Superabsorbent Polymer 11 g (110 ppm with respect to a monomer composition) of 0.5% IRGACURE 819 initiator diluted with acrylic acid and 26 g of 5% polyethyleneglycol diacrylate (PEGDA, a molecular weight of 400) diluted with acrylic acid were mixed to prepare a solution (solution A).

5% trimethylolpropane triacrylate containing 9 mol % of ethylene oxide (Ethoxylated-TMPTA, TMP(EO)9TA, M-3190 Miwon Specialty Chemical Co., Ltd.) diluted with acrylic acid was prepared as a solution B.

Into a 2 L-volume glass reactor surrounded by a jacket in which a heating medium pre-cooled to 25° C. was circulated, 37 g of the solution A and 14 g of the solution B were injected. To the glass reactor, 800 g of a 24% caustic soda solution (solution C) was slowly added dropwise and mixed. After confirming that the temperature of the mixed solution increased to about 72° C. or higher by neutralization heat upon adding dropwise the solution C, the mixed solution was left until it was cooled. A neutralization degree of acrylic acid in the mixed solution thus obtained was about 70 mol %.

Meanwhile, a 5% sodium bicarbonate solution diluted with water was prepared as a solution D, and 0.8 g of aluminium sulfate was dissolved in 28 g of 4% sodium persulfate solution diluted with water to prepare a solution E-2, and a 1% OFX-0193 (XIAMETER(R)) solution diluted with water was prepared as a solution F. 34 g of the solution D and 2.8 g of the solution F were mixed.

When the temperature of the mixed solution was cooled to about 45° C., the previously prepared solutions D and F were added to and mixed with the mixed solution, and the solution E-2 was added thereto at the same time.

Subsequently, the above-prepared mixed solution was poured in a Vat-type tray (15 cm in width×15 cm in length) installed in a square polymerizer which had a light irradiation device installed at the top and was preheated to 80° C., and the mixed solution was subjected to light irradiation. It was confirmed that at about 20 seconds after light irradiation, gel was generated from the surface, and at about 30 seconds after light irradiation, foam generation and polymerization occurred at the same time. Then, the reaction was allowed for additional 2 minutes, and the polymerized sheet was taken and cut in a size of 3 cm×3 cm, and then subjected to a chopping process using a meat chopper to prepare the cut sheet as crumbs.

Subsequently, the crumbs were dried in an oven capable of shifting airflow up and down. The crumbs were uniformly dried by flowing hot air at 180° C. from the bottom to the top for 15 minutes and from the top to the bottom for 15 minutes such that the dried crumbs had a water content of about 2% or less.

The dried crumbs were pulverized using a pulverizer and sorted by size, and a base polymer having a size of about 150 μm to about 850 μm was obtained. Centrifuge retention capacity of the base polymer thus obtained was 35.8 g/g, and a content of the water-soluble component was 13.7% by weight.

Thereafter, 100 g of the base polymer was mixed with a crosslinking agent solution which was prepared by mixing 3 g of water, 3 g of methanol, 0.4 g of ethylene carbonate, and 0.5 g of Aerosil 200 (EVONIK), and then surface crosslinking reaction was allowed at 190° C. for 30 minutes. The resulting product was pulverized and passed through a sieve to obtain a surface-crosslinked superabsorbent polymer having a particle size of 150 μm to 850 μm.

COMPARATIVE EXAMPLE 1

Preparation of Superabsorbent Polymer

A base polymer was prepared in the same manner as in Example 5, except that 28 g of a 4% sodium persulfate solution (solution E-0) diluted with water, instead of the mixture of the solutions D and F and the solution E-2, was added to the mixed solution in Example 5. Centrifuge retention capacity of the prepared base polymer was 39.3 g/g and a content of the water-soluble component was 19.3% by weight. The prepared base polymer was used to obtain a surface-crosslinked superabsorbent polymer having a particle size of 150 μm to 850 μm in the same manner as in Example 5.

COMPARATIVE EXAMPLE 2

Preparation of Superabsorbent Polymer

A base polymer was prepared in the same manner as in Comparative Example 1, except that 34 g of a 5% sodium bicarbonate solution (solution D) diluted with water was further added before adding the solution E-0 to the mixed solution in Comparative Example 1. Centrifuge retention capacity of the prepared base polymer was 34.2 g/g and a content of the water-soluble component was 13.1% by weight. The prepared base polymer was used to obtain a surface-crosslinked superabsorbent polymer having a particle size of 150 μm to 850 μm in the same manner as in Comparative Example 1.

COMPARATIVE EXAMPLE 3

Preparation of Superabsorbent Polymer

A base polymer was prepared in the same manner as in Example 1, except that a 1% OFX-0193 (XIAMETER(R)) solution diluted with acrylic acid as a surfactant was not added in Example 1. Centrifuge retention capacity of the prepared base polymer was 35.22 g/g. The prepared base polymer was used to obtain a surface-crosslinked superabsorbent polymer having a particle size of 150 μm to 850 μm in the same manner as in Example 1.

COMPARATIVE EXAMPLE 4

Preparation of Superabsorbent Polymer

A base polymer was prepared in the same manner as in Example 1, except that 28 g of a 4% sodium persulfate solution (solution E-0) diluted with water, instead of the solution (solution E-1) prepared by dissolving 1.6 g of aluminum sulfate in 28 g of 4% sodium persulfate solution diluted with water, was added to the mixed solution in Example 1. Centrifuge retention capacity of the prepared base polymer was 33.8 g/g. The prepared base polymer was used to obtain a surface-crosslinked superabsorbent polymer having a particle size of 150 μm to 850 μm in the same manner as in Example 1.

EXPERIMENTAL EXAMPLE

Evaluation of Superabsorbent Polymer

Properties of the superabsorbent polymers prepared in Examples 1 to 5 and Comparative Examples 1 to 4 were evaluated as follows, and shown in the following Table 1.

(1) Average Particle Size of Superabsorbent Polymer

The average particle sizes of the superabsorbent polymers prepared in Examples 1 to 5 and Comparative Examples 1 to 4 were measured according to European Disposables and Nonwovens Association standard EDANA WSP 220.2.

(2) Average Particle Size of Gel Obtained by Partially Swelling Superabsorbent Polymer The superabsorbent polymers prepared in Examples 1 to 5 and Comparative Examples 1 to 4 were partially swollen as follows.

1 g of the superabsorbent polymer was put in a plastic bag made of PE, and 20 g of 0.9% by weight of a physiological saline solution was injected thereto to swell the superabsorbent polymer for 10 minutes. Thereafter, 0.1 g of hydrophobic silica (trade name: DM-30S, manufacturer: Tokuyama) was added to the obtained gel (partially swollen superabsorbent polymer), and the plastic bag was shaken to uniformly apply silica onto the swollen superabsorbent polymer.

The hydrophobic silica was added to prevent a phenomenon, in which the gels stick to each other during measuring the average particle size thereof. Results of many experiments confirmed that the particle sizes of the gels were not changed by the addition and the addition amount of the hydrophobic silica.

The obtained average particle sizes of the gels were measured according to European Disposables and Nonwovens Association standard EDANA WSP 220.2.

(3) Centrifuge Retention Capacity (CRC)

Centrifuge retention capacity (CRC) in a physiological saline solution was measured for the superabsorbent polymers of Examples 1 to 5 and Comparative Examples 1 to 4 in accordance with EDANA method WSP 241.2.

In detail, among the superabsorbent polymers to be tested for centrifuge retention capacity, superabsorbent polymers having a particle size of 300 μm to 600 μm, which were passed through a US standard 30 mesh screen and retained on a US standard 50 mesh screen, were prepared.

The superabsorbent polymer $W_0$(g, about 0.2 g) having a particle size of 300 μm to 600 μm was uniformly placed into a nonwoven-fabric-made bag, followed by sealing. Then, the bag was immersed into 0.9% by weight of a physiological saline solution at room temperature. 30 minutes later, the bag was drained at 250 G for 3 minutes with a centrifuge, and the weight $W_2$(g) of the bag was then measured. Meanwhile, the same procedure was carried out using an empty bag having no superabsorbent polymer, and the resultant weight $W_1$(g) was measured.

Each of the weights thus obtained was used to confirm centrifuge retention capacity according to the following Equation 1:

$$CRC(g/g)=\{[W_2(g)-W_1(g)]/W_0(g)\}-1 \quad \text{[Calculation Formula 1]}$$

wherein $W_0$(g) is an initial weight (g) of the superabsorbent polymer having a particle size of 300 μm to 600 μm, $W_1$(g) is a weight of an apparatus which is measured after draining water off at 250 G for 3 minutes with a centrifuge without using the superabsorbent polymer, and $W_2$(g) is the weight of the apparatus including the superabsorbent polymer, which is measured after immersing the superabsorbent polymer in 0.9% by weight of the physiological saline solution at room temperature for 30 minutes and draining water off at 250 G for 3 minutes with a centrifuge.

(4) Absorbency Under Load (AUL)

Absorbency under load (AUL) of 0.9 psi in the physiological saline solution was measured for the superabsorbent polymers of Examples 1 to 5 and Comparative Examples 1 to 4 according to EDANA method WSP 242.2.

In detail, a 400 mesh stainless steel net was installed in the bottom of a plastic cylinder having an internal diameter of 25 mm. The superabsorbent polymer $W_0$(g, 0.16 g) to be tested for absorbency under load was uniformly scattered on the screen at room temperature and humidity of 50%. Subsequently, a piston which may uniformly provide a load of 6.3 kPa (0.9 psi) was put thereon, in which an external diameter of the piston was slightly smaller than 25 mm, there was no gab between the internal wall of the cylinder and the piston, and the jig-jog of the cylinder was not interrupted. At this time, the weight $W_3$(g) of the apparatus was measured.

After putting a glass filter having a diameter of 90 mm and a thickness of 5 mm in a petri dish having a diameter of 150 mm, a physiological saline solution of 0.9% by weight was poured in the dish until the surface level of the physiological saline solution became equal to the upper surface of the glass filter. A sheet of filter paper having a diameter of 90 mm was put on the glass filter.

Subsequently, the prepared apparatus was put on the filter paper and the superabsorbent polymer in the apparatus was allowed to swell by the physiological solution under a load. After 1 hr, the weight $W_4$(g) of the apparatus containing the swollen superabsorbent polymer was measured.

The weights thus obtained were used to calculate absorbency under load according to the following Equation 2:

$$AUL(g/g)=[W_4(g)-W_3(g)]/W_0(g) \quad \text{[Calculation Formula 2]}$$

wherein $W_0$(g) is an initial weight (g) of the superabsorbent polymer, $W_3$(g) is the sum of the weight of the superabsorbent polymer and the weight of the apparatus capable of providing a load for the superabsorbent polymer, and $W_4$(g) is the sum of the weight of the superabsorbent polymer after allowing the superabsorbent polymer to absorb the physiological saline solution under a load (0.9 psi) for 1 hour, and the weight of the apparatus capable of providing the load for the superabsorbent polymer.

(5) Gel Bed Permeability (GBP)

Free swell gel bed permeability (GBP) in a physiological saline solution was measured for the superabsorbent polymers of Examples 1 to 5 and Comparative Examples 1 to 4 according to the following method described in Patent Application. No. 2014-7018005.

In detail, an apparatus illustrated in FIGS. 1 to 3 was used to conduct a free swell GBP test. First, a plunger 536, with a weight 548 seated thereon, was placed in an empty sample container 530 and the height from the top of the weight 548 to the bottom of the sample container 530 was measured using a suitable gauge accurate to 0.01 mm. The force the thickness gauge applies during measurement was controlled to less than about 0.74 N.

Meanwhile, among the superabsorbent polymers to be tested for GBP, superabsorbent polymers, which were passed through a US standard 30 mesh screen and retained on a US standard 50 mesh screen, were selected to obtain the superabsorbent polymer having a particle size of 300 μm to 600 μm.

About 2.0 g of the size-sorted superabsorbent polymer was placed in a sample container 530 and spread out evenly on the bottom of the sample container. This container without the plunger 536 and weight 548 therein was then submerged in the 0.9% by weight of a physiological saline solution for about 60 minutes to allow the superabsorbent polymer to swell free of any restraining load. At this time, the sample container 530 was set on a mesh located in a liquid reservoir so that the sample container 530 was raised slightly above the bottom of a liquid reservoir. The mesh did not inhibit the flow of the physiological saline solution into the sample container 530. During saturation, a depth of the physiological saline solution was controlled such that the surface within the sample container was defined solely by the swollen superabsorbent polymer, rather than the physiological saline solution.

At the end of this period, the plunger 536 and weight 548 assembly was placed on the swollen superabsorbent polymer 568 in the sample container 530 and then the sample container 530, plunger 536, weight 548, and swollen superabsorbent polymer 568 were removed from the solution. Then, before GBP measurement, the sample container 530, plunger 536, weight 548, and swollen superabsorbent polymer 568 were to remain at rest for about 30 seconds on a large grid non-deformable plate of uniform thickness. The height from the top of the weight 548 to the bottom of the sample container 530 was measured again by using the same thickness gauge used previously. The height measurement of the apparatus where the plunger 536 and the weight 548 were placed in the empty sample container 530 was subtracted from the height measurement of the apparatus containing the swollen superabsorbent polymer 568 to obtain the thickness or height "H" of the swollen superabsorbent polymer.

For GBP measurement, a flow of 0.9% physiological saline solution was delivered into the sample container 530 with the swollen superabsorbent polymer 568, plunger 536, and weight 548 inside. The flow rate of the physiological saline solution into the sample container 530 was adjusted to cause the physiological saline solution to overflow the top of the cylinder 534, resulting in a consistent head pressure equal to the height of the sample container 530. The quantity of solution passing through the swollen superabsorbent polymer 568 versus time was measured gravimetrically using a scale 602 and a beaker 603. Data points from the scale 602 were collected every second for at least 60 seconds once the overflow has begun. The flow rate, Q through the swollen superabsorbent polymer 568 was determined in units of g/sec by a linear least-square fit of fluid (g) passing through the swollen superabsorbent polymer 568 versus time (sec).

GBP (cm$^2$) was calculated from the obtained data according to the following Calculation Formula 3:

$$K=[Q*H*\mu]/[A*\rho*P]$$ [Calculation Formula 3]

wherein K is gel bed permeability (cm$^2$),

Q is a flow rate (g/sec),

H is a height of swollen sample (cm), $\mu$ is liquid viscosity (P) (viscosity of the physiological saline solution used in this test was about 1 cp), A is a cross-sectional area for liquid flow (28.27 cm$^2$ for the sample container used in this test), $\rho$ is a liquid density (g/cm$^3$) (about 1 g/cm$^3$ for the physiological saline solution used in this test), and P is a hydrostatic pressure (dynes/cm$^2$) (normally about 7.797 dynes/cm$^2$).

The hydrostatic pressure is calculated from $P=\rho*g*h$, wherein $\rho$ is a liquid density (g/cm$^3$), g is gravitational acceleration (nominally 981 cm/sec$^2$), and h is a fluid height (e.g., 7.95 cm for the GBP test described herein).

At least two samples were tested, and an average of the results was determined as free swell GBP of the superabsorbent polymer, and the unit was converted to darcy (1 darcy=0.98692×10$^{-8}$ cm$^2$) and shown in Table 1.

(6) Absorption Rate (Vortex Time) of Superabsorbent Polymer

The absorption rates of the superabsorbent polymers of Examples 1 to 5 and Comparative Examples 1 to 4 were measured in seconds in accordance with a method described in International Patent Application No. 1987-003208.

In detail, the absorption rate (or vortex time) was calculated by measuring a time which was required until the vortex disappears, after adding 2 g of the superabsorbent polymer to 50 mL of a physiological saline solution and then agitating it at 600 rpm.

(7) Rewetting Property of Superabsorbent Polymer

The rewetting properties of the superabsorbent polymers of Examples 1 to 5 and Comparative Examples 1 to 4 were evaluated by modifying the previously known method of measuring absorbency under load.

First, among the superabsorbent polymers to be tested for the rewetting property, superabsorbent polymers having a particle size of 300 μm to 600 μm, which were passed through a US standard 30 mesh screen and retained on a US standard 50 mesh screen, were prepared.

Meanwhile, a 400 mesh stainless steel screen was installed in the bottom of a plastic cylinder having an internal diameter of 25 mm. The superabsorbent polymer $W_0$(g, 0.16 g) previously prepared was uniformly scattered on the screen at room temperature and humidity of 50% to prepare a test assembly.

Subsequently, a first filter paper of 25 mm in diameter was placed in a PE dish of 80 mm in diameter, and the test assembly was placed thereon. Thereafter, 4 g of 0.9% by weight of a physiological saline solution was injected around the test assembly, and the superabsorbent polymer was allowed to absorb the physiological saline solution under no load. After all the physiological saline solution was absorbed by the superabsorbent polymer, the superabsorbent polymer was left for 10 minutes to be sufficiently swollen.

Meanwhile, 10 filter papers of 30 mm or more in diameter, which were Whatman No. 4 filter papers, were overlapped to prepare a second filter paper. The weight $W_5$(g) of the second filter paper was measured.

After the test assembly was separated from the first filter paper, a piston which may uniformly provide a load of 5.1 kPa (0.7 psi) for the swollen superabsorbent polymer was put thereon, in which an external diameter of the piston was slightly smaller than 25 mm, there was no gab between the internal wall of the cylinder and the piston, and the jig-jog of the cylinder was not interrupted.

The test assembly, to which the piston was applied, was placed on the second filter paper previously prepared. 2 minutes later, after lifting and separating the test assembly, to which the piston was applied, the weight $W_6$(g) of the second filter paper was measured again.

Each of the weights thus obtained was used to calculate the rewetting amount (g/g) according to the following Calculation Formula 4:

$$\text{Rewetting amount }(g/g)=[W_0(g)-W_5(g)]/W_0(g)$$ [Calculation Formula 4]

wherein $W_0$(g) is an initial weight (g) of the superabsorbent polymer, $W_5$(g) is an initial weight (g) of the second filter paper, and $W_6$(g) is the weight of the second filter paper which absorbed liquid leaking from the swollen superabsorbent polymer under a load (0.7 psi) for 2 minutes after allowing the superabsorbent polymer to absorb 25 times volume of the physiological saline solution under no load for a sufficient time.

TABLE 1

|  | Average particle size of superabsorbent polymer [μm] | Average particle size of gel [μm] | CRC [g/g] | AUL [g/g] | GBP [darcy] | Vortex time [sec] | Rewetting amount [g/g] |
|---|---|---|---|---|---|---|---|
| Example 1 | 424 | 870 | 30.7 | 19.7 | 57 | 35 | 0.4 |
| Example 2 | 458 | 835 | 30.1 | 19.4 | 53 | 37 | 0.6 |
| Example 3 | 428 | 943 | 30.4 | 19.1 | 75 | 32 | 0.5 |
| Example 4 | 380 | 840 | 30.8 | 19.5 | 62 | 40 | 0.7 |
| Example 5 | 375 | 825 | 30.3 | 19.9 | 63 | 39 | 0.7 |
| Comparative Example 1 | 476 | 1237 | 31.1 | 18.7 | 60 | 85 | 1.8 |
| Comparative Example 2 | 384 | 546 | 30.1 | 17.3 | 56 | 45 | 1.5 |
| Comparative Example 3 | 460 | 1120 | 31.8 | 16.5 | 53 | 92 | 2.2 |
| Comparative Example 4 | 472 | 1180 | 29.5 | 18.3 | 48 | 74 | 1.6 |

(8) Particle Size Distribution of Gel

The superabsorbent polymer prepared in Example 1 was partially swollen in the same manner as in the method of (2), in which the superabsorbent polymer was partially swollen in order to measure the average particle sizes of the gels, and an equal amount of the same silica was added to the obtained gels.

The gels obtained as above were size-sorted by different meshes (Mesh #14, Mesh #18, Mesh #20, and Mesh #30). First, the gels were sorted by Mesh #14 into particles having a particle size of more than 1400 μm and particles having a particle size of 1400 μm or less. The particles having a particle size of 1400 μm or less were sorted by Mesh #18 into particles having a particle size of more than 1000 μm and 1400 μm or less and particles having a particle size of 1000 μm or less. The particles having a particle size of 1000 μm or less were sorted by Mesh #20 into particles having a particle size of more than 850 μm and 1000 μm or less and particles having a particle size of 850 μm or less. Lastly, the particles having a particle size of 850 μm or less were sorted by Mesh #30 into particles having a particle size of more than 600 μm and 800 μm or less and particles having a particle size of 600 μm or less. In this regard, the sorting conditions were controlled to be 1.0 AMP and 2 minutes.

The gels were sorted as above, and the weights and fractions of the gels belonging to the particle size range in Table 2 were obtained. The results are shown in Table 2.

TABLE 2

| | | Particle size [μm] | | | | |
|---|---|---|---|---|---|---|
| | | More than 1400 | More than 1000 and 1400 or less | More than 850 and 1000 or less | More than 600 and 850 or less | 600 or less |
| Example 1 | Weight [g] | 3.1 | 7.6 | 4.1 | 3.6 | 3.9 |
| | Fraction [wt %] | 13.9 | 34.1 | 18.4 | 16.1 | 17.5 |

REFERENCE NUMERALS

500: GBP measuring apparatus
528: Test apparatus assembly
530: Sample container
534: Cylinder
534a: Region with outer diameter of 66 mm
536: Plunger
538: Shaft
540: O-ring
544, 554, 560: Holes
548: Annular weight
548a: Thru-bore
550: Plunger head
562: Shaft hole
564: Stainless steel cloth screen of 100 mesh
566: Stainless steel cloth screen of 400 mesh
568: Sample
600: Weir
601: Collection device
602: Scale
603: Beaker
604: Metering pump

The invention claimed is:

1. A superabsorbent polymer having an average particle size of 300 μm to 600 μm, wherein the superabsorbent polymer is configured to become a gel having an average particle size of 600 μm to 1000 μm, when 1 g of the superabsorbent polymer is swelled in 20 g of 0.9% by weight of a sodium chloride aqueous solution for 10 minutes, wherein the superabsorbent polymer is prepared by:

performing crosslinking polymerization of a monomer mixture in the presence of an internal crosslinking agent to form a water-containing gel polymer, the monomer mixture including water-soluble ethylene-based unsaturated monomers having acidic groups which are at least partially neutralized, a foaming agent, a foam promoter, and a surfactant;

drying, pulverizing, and size-sorting the water-containing gel polymer to form a base polymer powder; and additionally crosslinking the surface of the base polymer powder in the presence of a surface crosslinking agent to form a surface-crosslinked layer, wherein the foaming agent is included in an amount of about 0.05% by weight to about 5.0% by weight with respect to a total weight of the monomer mixture, the foam promoter is included in an amount of about 0.01% by weight to about 3% by weight with respect to the total weight of the monomer mixture, and the surfactant is included in an amount of about 0.001% by weight to about 1% by weight with respect to the total weight of the monomer mixture, and wherein the foam promoter is an inorganic acid aluminum salt and/or an organic acid aluminum salt.

2. The superabsorbent polymer of claim 1, wherein a particle having a particle size of 300 μm to 600 μm is 45% by weight to 85% by weight.

3. The superabsorbent polymer of claim 1, wherein a particle having a particle size of more than 0 μm and 300 μm or less is 15% by weight to 25% by weight.

4. The superabsorbent polymer of claim 1, wherein a fraction of a gel having a particle size of more than 0 μm and 600 μm or less is 5% by weight to 30% by weight.

5. The superabsorbent polymer of claim 1, wherein centrifuge retention capacity in a physiological saline solution is 28 g/g to 35 g/g, absorbency under load of 0.9 psi in the physiological saline solution is 14 g/g to 22 g/g, free swell gel bed permeability in the physiological saline solution is 40 darcy to 100 darcy, and a vortex time is 20 seconds to 60 seconds.

6. A preparation method for preparing the superabsorbent polymer of claim 1, comprising:

performing crosslinking polymerization of a monomer mixture in the presence of an internal crosslinking agent to form a water-containing gel polymer, the monomer mixture including water-soluble ethylene-based unsaturated monomers having acidic groups which are at least partially neutralized, a foaming agent, a foam promoter, and a surfactant;

drying, pulverizing, and size-sorting the water-containing gel polymer to form a base polymer powder; and additionally crosslinking the surface of the base polymer powder in the presence of a surface crosslinking agent to form a surface-crosslinked layer, wherein the foaming agent is included in an amount of about 0.05% by weight to about 5.0% by weight with respect to a total weight of the monomer mixture, the foam promoter is included in an amount of about 0.01% by weight to about 3% by weight with respect to the total weight of the monomer mixture, and the surfactant is included in an amount of about 0.001% by weight to about 1% by weight with respect to the total weight of the monomer mixture, and wherein the foam promoter is an inorganic acid aluminum salt and/or an organic acid aluminum salt.

7. The preparation method of claim 6, wherein one or more selected from the group consisting of magnesium carbonate, calcium carbonate, sodium bicarbonate, sodium carbonate, potassium bicarbonate, and potassium carbonate are used as the foaming agent.

8. The preparation method of claim 6, wherein polysiloxane with polyether side chains is used as the surfactant.

* * * * *